US011252496B2

(12) United States Patent
Raft

(10) Patent No.: US 11,252,496 B2
(45) Date of Patent: Feb. 15, 2022

(54) HEARING PROTECTION DEVICE WITH PASSIVE EAR PROTECTORS

(71) Applicant: GN HEARING A/S, Ballerup (DK)

(72) Inventor: Casper Silbo Raft, Ballerup (DK)

(73) Assignee: GN HEARING A/S, Ballerup (DK)

(*) Notice: Subject to any disclaimer, the term of this patent is extended or adjusted under 35 U.S.C. 154(b) by 0 days.

(21) Appl. No.: 16/526,861

(22) Filed: Jul. 30, 2019

(65) Prior Publication Data
US 2020/0100016 A1 Mar. 26, 2020

(30) Foreign Application Priority Data

Sep. 25, 2018 (EP) .................................. 18196635
Apr. 24, 2019 (EP) .................................. 19170890

(51) Int. Cl.
H04R 1/10 (2006.01)
H04W 4/80 (2018.01)
(Continued)

(52) U.S. Cl.
CPC ............ H04R 1/1083 (2013.01); A61F 11/14 (2013.01); G06F 3/165 (2013.01);
(Continued)

(58) Field of Classification Search
CPC .. H04R 1/0183; H04R 1/1016; H04R 1/1008; G10K 2210/108; G10K 2210/1081;
(Continued)

(56) References Cited

U.S. PATENT DOCUMENTS 3,952,158 A * 4/1976 Kyle .................. H04R 3/04
381/72
5,426,719 A * 6/1995 Franks ................ H04R 1/1083
381/72
(Continued)

FOREIGN PATENT DOCUMENTS

WO WO 98/41974 A2 9/1998
WO WO 98/41974 A3 9/1998

OTHER PUBLICATIONS

Extended European Search Report dated Mar. 20, 2019 for corresponding European Application No. 18196635.9.
(Continued)

Primary Examiner — Xu Mei
(74) Attorney, Agent, or Firm — Vista IP Law Group, LLP

(57) ABSTRACT

A hearing protection system comprising a hearing protection device and a communication device is disclosed, the hearing protection device comprising a first connector; a first ear protector comprising a first sound attenuation body, a first primary microphone, and a first receiver, wherein the first primary microphone and the first receiver are electrically connected to a first primary terminal and a first receiver terminal of the first connector, respectively, and wherein the first sound attenuation body is configured to cover an outer ear of a user; and a second ear protector comprising a second sound attenuation body, a second primary microphone, and a second receiver, wherein the second primary microphone and the second receiver are electrically connected to a second primary terminal and a second receiver terminal of the first connector, respectively, and wherein the second sound attenuation body is configured to cover an outer ear of a user.

45 Claims, 7 Drawing Sheets

(51) Int. Cl.
*A61F 11/14* (2006.01)
*G06F 3/16* (2006.01)
*G10L 21/0232* (2013.01)
*H04R 1/08* (2006.01)
*H04R 1/40* (2006.01)
*H04R 3/00* (2006.01)

(52) U.S. Cl.
CPC ............ *G10L 21/0232* (2013.01); *H04R 1/08* (2013.01); *H04R 1/1008* (2013.01); *H04R 1/406* (2013.01); *H04R 3/005* (2013.01); *H04W 4/80* (2018.02); *A61F 2011/145* (2013.01)

(58) Field of Classification Search
CPC .. A61F 2/08; A61F 11/06; A61F 11/08; A61F 2011/145; A61F 2011/085
USPC .................................. 381/72, 73.1, 74, 71.6
See application file for complete search history.

(56) References Cited

U.S. PATENT DOCUMENTS

| | | | |
|---|---|---|---|
| 5,673,325 A * | 9/1997 | Andrea | H04M 1/05 381/92 |
| 8,243,942 B2 * | 8/2012 | Grandt | H04R 1/1083 381/71.6 |
| 8,243,943 B2 * | 8/2012 | Nordin | H04R 1/1083 381/72 |
| 8,280,066 B2 | 10/2012 | Joho et al. | |
| 9,628,897 B2 | 4/2017 | Fletcher et al. | |
| 2001/0050993 A1 * | 12/2001 | Douglas | G10K 11/178 381/71.6 |
| 2011/0268295 A1 | 11/2011 | Yamkovoy et al. | |
| 2011/0286608 A1 | 11/2011 | Hautier et al. | |
| 2012/0063622 A1 * | 3/2012 | Bruckhoff | A61F 11/008 381/328 |
| 2014/0198926 A1 * | 7/2014 | Killion | H04R 1/1041 381/72 |
| 2019/0230431 A1 * | 7/2019 | Raft | A61F 2/08 |

OTHER PUBLICATIONS

Third party observations dated Mar. 1, 2021 filed for European patent application No. 19170890.8.

\* cited by examiner

HEARING PROTECTION DEVICE WITH PASSIVE EAR PROTECTORS

RELATED APPLICATION DATA

This application claims priority to, and the benefit of, European Patent Application No. 18196635.9 filed on Sep. 25, 2018, and European Patent Application No. 19170890.8 filed on Apr. 24, 2019. The disclosures of both of the above applications are expressly incorporated by reference herein.

FIELD

The present disclosure relates to a hearing protection device, a communication device, and a hearing protection system comprising the hearing protection device.

BACKGROUND

In combat situations and/or noisy environments, it is desirable for a user to effectively protect his/her hearing while enabling the user to communicate with others both via face to face communication and via radio or other communication system. During combat situations and/or in noisy environments, a user may need to wear a hearing protector, to attenuate noise from gunfire, machinery and other types of constant or intermittent noise.

A drawback of using a hearing protection device is that normal sounds, such as speech, or other environmental sounds may be attenuated, causing the user to struggle in hearing what is going on around him. One solution for this has been to provide the hearing protection device with simple active processing devices with batteries arranged in the ear protectors of the hearing protector in turn requiring tedious and cumbersome handling and maintenance.

SUMMARY

Accordingly, there is a need for hearing protection devices and systems that are easy to handle and maintain.

A hearing protection device is disclosed, the hearing protection device comprising a first connector; a first ear protector comprising a first sound attenuation body, a first primary microphone, and a first receiver, wherein the first primary microphone and the first receiver are electrically connected to a first primary terminal and a first receiver terminal of the first connector, respectively, and wherein the first sound attenuation body is configured to cover an outer ear of a user; and a second ear protector comprising a second sound attenuation body, a second primary microphone, and a second receiver, wherein the second primary microphone and the second receiver are electrically connected to a second primary terminal and a second receiver terminal of the first connector, respectively, and wherein the second sound attenuation body is configured to cover an outer ear of the user, i.e. the user of the hearing protection device.

Also disclosed is a communication device and a hearing protection system comprising the hearing protection device and the communication device.

A hearing protection system comprising a hearing protection device and a communication device is disclosed, wherein the hearing protection device comprises a first connector; a first ear protector comprising a first sound attenuation body, a first primary microphone, and a first receiver, wherein the first primary microphone and the first receiver are electrically connected to a first primary terminal and a first receiver terminal of the first connector, respectively, and wherein the first sound attenuation body is configured to cover an outer ear of a user; and a second ear protector comprising a second sound attenuation body, a second primary microphone, and a second receiver, wherein the second primary microphone and the second receiver are electrically connected to a second primary terminal and a second receiver terminal of the first connector, respectively, and wherein the second sound attenuation body is configured to cover an outer ear of a user, and wherein communication device comprises an interface including a second connector comprising terminals configured for mating with respective terminals of the first connector of the hearing protection device, the communication device comprising a processor configured to: receive a first primary microphone input signal from the first primary microphone; process the first primary microphone input signal for provision of a first output signal for the first receiver based on the first primary microphone input signal, wherein to process the first primary microphone input signal comprises applying noise reduction to the first primary microphone input signal; and output the first output signal to a first receiver terminal of the second connector.

It is an important advantage of the hearing protection device that a hearing protection device with improved flexibility during use is provided. The present hearing protection device allows for easy switching between an earmuff hearing protection device and an earpiece hearing protection device.

The disclosed hearing protection device and hearing protection system is easy to handle and maintain.

Further, the present disclosure allows for improved and complex hearing protection processing due to processing being performed in a communication device.

It is an advantage of the present disclosure that an effective passive (mechanical) sound attenuation is provided with the ear protectors given an available ear protector volume, while at the same time allowing for improved hear-through processing and communication with external devices.

BRIEF DESCRIPTION OF THE DRAWINGS

The above and other features and advantages of the embodiments will become readily apparent to those skilled in the art by the following detailed description of exemplary embodiments thereof with reference to the attached drawings, in which.

DETAILED DESCRIPTION

Figure 1:
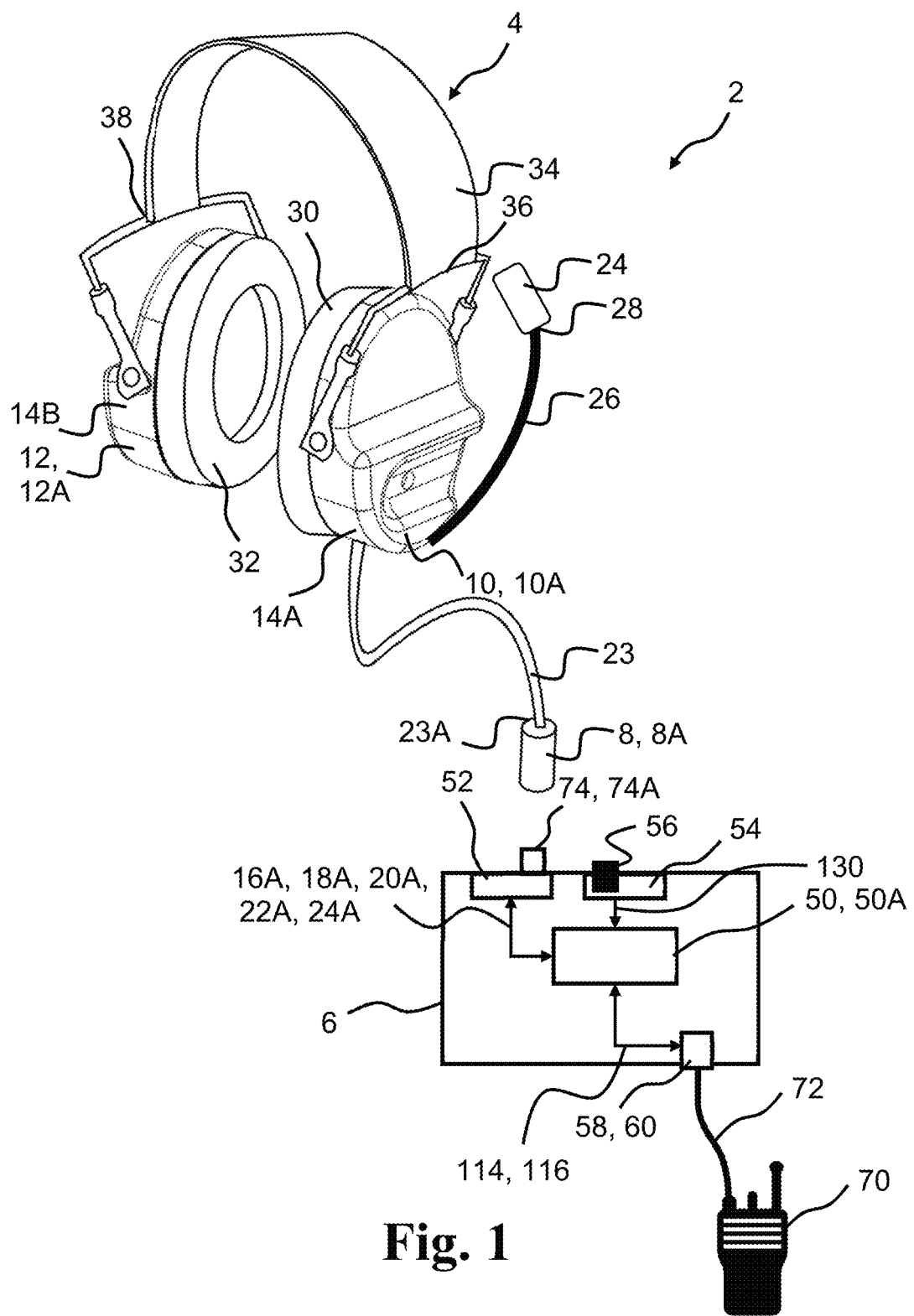
FIG. 1 schematically illustrates an exemplary hearing protection system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing protection device, a communication device, and a hearing protection system comprising a hearing protection device and a communication device is disclosed.

The hearing protection device comprises a first connector. The first connector comprises a number of terminals, such as at least four terminals or at least ten terminals. The first connector comprises a first primary terminal and a first receiver terminal. The first connector optionally comprises a second primary terminal and a second receiver terminal. The first connector optionally comprises a secondary terminal. The first connector may comprise a first secondary terminal and/or a second secondary terminal. The first connector may comprise one or more reference terminals, such as a common reference (ground) terminal. The first connector may comprise a first reference terminal and a second reference terminal. The first reference terminal may form a reference for the microphones of the hearing protection device or a reference for components of the first ear protector. The second reference terminal may form a reference for the receivers of the hearing protection device or a reference for components of the second ear protector.

The hearing protection device comprises a first ear protector. The first ear protector comprises a first sound attenuation body, a first primary microphone, and a first receiver, wherein the first primary microphone and the first receiver are electrically connected to a first primary terminal and a first receiver terminal of the first connector, respectively. The first sound attenuation body is configured to cover an outer ear or at least a part of an outer ear of a user. The first ear protector optionally comprises a first cushion configured to encircle an outer ear of the user. The first ear protector may be an earmuff.

The hearing protection device comprises a second ear protector. The second ear protector comprises a second sound attenuation body, a second primary microphone, and a second receiver, wherein the second primary microphone and the second receiver are electrically connected to a second primary terminal and a second receiver terminal of the first connector, respectively. The second sound attenuation body is configured to cover an outer ear or at least a part of an outer ear of a user. The second ear protector may be an earmuff.

The first primary microphone device and the second primary microphone device are configured to receive sound from the surroundings. The first receiver and the second receiver are configured for outputting audio or sound signals towards the respective ears of the user when the hearing protection device is in use.

In one or more exemplary hearing protection devices, the hearing protection device comprises a secondary microphone device electrically connected to a secondary terminal of the first connector. The secondary microphone device may be configured for picking up own voice of a user of the hearing protection device. For example, the hearing protection device optionally comprises a microphone boom with a distal end. The secondary microphone device may be arranged at the distal end of the microphone boom. The secondary microphone device comprises on or more microphones and is configured to provide a secondary microphone input signal on the secondary terminal of the first connector. The secondary microphone device and the microphone boom may be collectively referred to as a secondary microphone assembly, e.g. a first secondary microphone device. The second ear protector optionally comprises a second cushion configured to encircle an outer ear of the user.

The hearing protection device may comprise one or more secondary microphone assemblies including a first secondary microphone assembly and/or a second secondary microphone assembly. The first secondary microphone assembly may comprise a secondary microphone device and a microphone boom. The second secondary microphone assembly may be configured for chemical warfare, e.g. embedded in a gas mask or other respiratory protection. The first secondary microphone assembly may be of a first type. The second secondary microphone assembly may be of a second type.

The first ear protector may comprise a first boom connector for connecting a secondary microphone assembly to the first ear protector. The second ear protector may comprise a second boom connector for connecting a secondary microphone assembly to the second ear protector. Having a boom connector in both the first ear protector (first boom connector) and/or the second ear protector (second boom connector) allows for a user to easily fit the hearing protection device to his/her personal needs. For example, the hearing protection device with secondary microphone assembly can be easily adjusted or fitted to both a left handed shooter and a right handed shooter, in turn reducing the stock costs and/or increasing the flexibility in handling and managing an inventory of hearing protection devices. Further, a boom connector allows for easy replacement of a malfunctioning and/or wrong-sized secondary microphone assembly. The boom connector(s), such as the first boom connector and/or the second boom connector, allows for use of different types of secondary microphone assemblies, e.g. depending on the use of the hearing protection device, in turn heavily increasing the flexibility during use.

A secondary microphone assembly comprises a connector for connecting the secondary microphone assembly to a boom connector, e.g. the first boom connector and/or the second boom connector.

A boom connector may comprise one or more guide elements and/or guide members. A connector of a secondary microphone assembly may comprise one or more guide elements and/or guide members. A boom connector, such as first boom connector and/or second boom connector, may be configured to guide, releasably fix and/or lock the secondary microphone assembly in a desired position, e.g. to ensure correct mounting and/or positioning of the secondary microphone assembly.

Each boom connector comprises one or more microphone terminals for mating with respective microphone terminals of the connector of secondary microphone assembly. Each boom connector comprises a ground or reference terminal for mating with respective ground or reference terminal of the connector of secondary microphone assembly. The ground terminal(s) of the first boom connector and/or the second boom connector is/are wired to ground or reference terminal of the first connector. A first microphone terminal of the first boom connector may be wired to a first secondary terminal of the first connector. A first microphone terminal of the second boom connector may be wired to a second secondary terminal of the first connector. In one or more exemplary hearing protection devices, the first microphone terminals of the first boom connector and the second boom connector are wired to the same secondary terminal of the first connector, e.g. via a switch.

The hearing protection device may be a passive hearing protection device. A passive hearing protection device is a hearing protection device with no internal power source. A passive hearing protection device allows for a simple ear protector with increased available volume in ear protectors for dampening of sound.

In one or more exemplary hearing protection devices, the first ear protector comprises a first attachment assembly, wherein the first attachment assembly is configured for attachment to a helmet. The second ear protector optionally comprises a second attachment assembly, wherein the second attachment assembly is configured for attachment to a helmet.

The hearing protection device may comprise a headband. The first ear protector may be connected or connectable to a first end of the headband. The second ear protector may be connected or connectable to a second end of the headband.

A communication device is disclosed. The communication device comprises an interface including a second connector comprising terminals configured for mating with respective terminals of the first connector of the hearing protection device.

The second connector comprises a number of terminals, such as at least four terminals or at least ten terminals. The second connector comprises a first primary terminal and a first receiver terminal. The second connector optionally comprises a second primary terminal and a second receiver terminal. The second connector optionally comprises a secondary terminal. The second connector may comprise a first secondary terminal and/or a second secondary terminal. The secondary terminal(s) of the second connector are configured to mate with or contact corresponding secondary terminal(s) of the first connector.

The interface of the communication device comprises a hearing protection device interface including the second connector for connection to the hearing protection device.

The interface of the communication device may comprise a user interface including one or more buttons, such as a first button, and optionally a radio interface. The first button of the user interface may be configured as a push-to-talk button. The radio interface is configured for connection to a radio unit or a communication system/intercom system. The radio interface may include a third connector for connecting to and communicating with a radio unit or a central communication system/intercom system via a cable.

The third connector may comprise a power terminal for provision of power to the communication device from a power unit, e.g. a battery, of the radio unit or communication system/intercom system when connected to the third connector. Accordingly, the hearing protection system may be configured for receiving power from a radio unit or intercom system via the third connector. This is highly beneficial, since charging of batteries and/or exchange of batteries is not necessary for the hearing protection system, but moved to the radio unit/intercom system, in turn making handling and operation of the hearing protection device/system easier and more reliable.

The communication device optionally comprises a processor. The processor is wired to respective terminals of the hearing protection device interface, the user interface, and the radio interface. The processor may be configured to receive a first primary microphone input signal from the first primary microphone; process the first primary microphone input signal for provision of a first output signal for the first receiver based on the first primary microphone input signal; and output the first output signal to a first receiver terminal of the second connector. By having signal processing taking place in the communication device, a more complex and sophisticated signal processing can take place while allowing for a reduced-size ear protector and/or improved mechanical noise reduction in the ear protector. Further, the same hearing protection device can be readily used for different/next-generation communication devices.

In the processor of the communication device, to process the first primary microphone input signal may comprise performing hear-through processing of the first primary microphone input signal. In the present context hear-through processing is signal processing which improves or adjusts the properties of the input signal for the benefit of the user. In other words, hear-through processing is the ability for the user to hear the surrounding environment, while being protected by the hearing protection system. The hear-through path is the electrical path from the external microphone (first primary microphone and second primary microphone) through the processor and which is then played in the receiver (first receiver and second receiver).

In the processor of the communication device, to process the first primary microphone input signal may comprise, e.g. as part of performing hear-through processing of the first primary microphone input signal, applying noise reduction, e.g. impulse noise reduction and/or broadband noise reduction, to the first primary microphone input signal. Applying noise reduction to the first primary microphone input signal may comprise applying noise reduction to selected frequency bands, such as one, two, three, or more frequency bands, of the first primary microphone input signal.

In one or more exemplary communication devices, the processor may be configured to receive a second primary microphone input signal from the second primary microphone; process the second primary microphone input signal for provision of a second output signal for the second receiver based on the second primary microphone input signal; and output the second output signal to a second receiver terminal of the second connector.

In the processor of the communication device, to process the second primary microphone input signal may comprise performing hear-through processing of the second primary microphone input signal.

In the processor of the communication device, to process the second primary microphone input signal may comprise, e.g. as part of performing hear-through processing of the second primary microphone input signal, applying noise reduction, e.g. impulse noise reduction and/or broadband noise reduction, to the second primary microphone input signal. Applying noise reduction to the second primary microphone input signal may comprise applying noise reduction to selected frequency bands, such as one, two, three, or more frequency bands, of the second primary microphone input signal.

Accordingly, the processor may comprise a hear-through processing module for hear-through processing of the first primary microphone input signal and/or the second primary microphone input signal. The processor, e.g. as part of hear-through processing module, may comprise a first noise reduction module for performing noise reduction, such as impulse noise reduction and/or broadband noise reduction, on the first primary microphone input signal, e.g. for provision of a first primary output signal forming at least part of the first output signal for the first receiver based on the first primary microphone input signal. The processor, e.g. as part of hear-through processing module, may comprise a second noise reduction module for performing noise reduction, such as impulse noise reduction and/or broadband noise reduction, on the second primary microphone input signal, e.g. for provision of second primary output signal forming at least part of second output signal for the second receiver based on the second primary microphone input signal.

In one or more exemplary communication devices, the processor may be configured to receive a secondary microphone input signal from the secondary microphone device; process the secondary microphone input signal for provision of an output audio signal based on the secondary microphone input signal; and output the output audio signal, e.g. to an audio terminal of the radio interface. Thereby, the communication device is able to pick-up and transmit to a radio unit own voice of a user of the hearing protection device.

In one or more exemplary communication devices, the processor may be configured to determine if one or more microphone criteria are met, and, in accordance with one or more microphone criteria being satisfied, process the secondary microphone input signal for provision of an output audio signal based on the secondary microphone input signal; and output the output audio signal, e.g. to an audio terminal of the radio interface.

In one or more exemplary communication devices, to determine if one or more microphone criteria are met comprises to determine if the secondary microphone assembly is of a first type, and in accordance with determining that the secondary microphone assembly is of the first type (first secondary microphone assembly), process the secondary microphone input signal according to a first processing scheme.

In one or more exemplary communication devices, to determine if one or more microphone criteria are met comprises to determine if the secondary microphone assembly is of a second type, and in accordance with determining that the secondary microphone assembly is of the second type (second secondary microphone assembly), process the secondary microphone input signal according to a second processing scheme. The second processing scheme may be different from the first processing scheme, e.g. different filters and/or gains may be applied in the first processing scheme and the second processing scheme.

In one or more exemplary communication devices, to determine if one or more microphone criteria are met comprises to determine a type of the secondary microphone assembly from a set of types, and process the secondary microphone input signal according to the type of the secondary microphone assembly.

In one or more exemplary communication devices, to determine if one or more microphone criteria are met comprises to determine if a secondary microphone assembly is connected to the first boom connector of the hearing protection device, and in accordance with determining that the secondary microphone assembly is connected to the first boom connector, process the secondary microphone input signal according to a processing scheme based on the secondary microphone assembly being connected to the first boom connector. To determine if a secondary microphone assembly is connected to the first boom connector of the hearing protection device may comprise determining a first impedance, a first resistance or other electronic property between two terminals of the second connector, such as between a reference terminal and a (first) secondary terminal of the second connector. The secondary microphone assembly may be determined to be connected to the first boom connector if the first impedance satisfies a first connection criterion, e.g. if the first impedance is less than a first connection threshold. Different types of secondary microphone assemblies may have different impedances, such as different resistances and thereby the communication device may be able to distinguish between different types of secondary microphone assemblies.

In one or more exemplary communication devices, to determine if one or more microphone criteria are met comprises to determine if a secondary microphone assembly is connected to the second boom connector of the hearing protection device, and in accordance with determining that the secondary microphone assembly is connected to the second boom connector, process the secondary microphone input signal according to a processing scheme based on the secondary microphone assembly being connected to the second boom connector. To determine if a secondary microphone assembly is connected to the second boom connector of the hearing protection device may comprise determining a second impedance, a second resistance or other electronic property between two terminals of the second connector, such as between a reference terminal and a (second) secondary terminal of the second connector. The secondary microphone assembly may be determined to be connected to the second boom connector if the second impedance satisfies a second connection criterion, e.g. if the second impedance is less than a second connection threshold.

In one or more exemplary communication devices, to determine if one or more microphone criteria are met comprises to determine if no secondary microphone assembly is connected to the first boom connector or the second boom connector of the hearing protection device, and in accordance with determining that no secondary microphone assembly is connected to the first boom connector or the second boom connector, forgoing to process the secondary microphone input signal. To determine if no secondary microphone assembly is connected to the first boom connector or to the second boom connector of the hearing protection device may comprise determining a first impedance and a second impedance respectively between two terminals of the second connector. The processor may determine that no secondary microphone assembly is connected to the first boom connector or the second boom connector if the first impedance satisfies a first disconnection criterion and the second impedance satisfies a second disconnection criterion. The first disconnection criterion may be satisfied if the first impedance is larger than a first disconnection threshold. The second disconnection criterion may be satisfied if the second impedance is larger than a second disconnection threshold.

Thus, the processing of secondary microphone input signal may be automatically adjusted to and being dependent on which boom connector of the hearing protection device if any being currently used. This is highly advantageous in reducing cumbersome setup of the hearing protection system when changing the secondary microphone assembly and/or switching position (boom connector) of the secondary microphone assembly. Further, secondary microphone assemblies from different manufacturers may be used with the present hearing protection device optionally via a simple adapter.

Detection of position (first or second boom connector) and type of the secondary microphone assembly may be combined to select a processing scheme configured or adjusted to both position and type of the secondary microphone assembly.

In one or more exemplary communication devices, to determine if one or more microphone criteria are met comprises to determine if a secondary microphone assembly of a first type (first secondary microphone assembly) is connected to the first boom connector of the hearing protection device, and in accordance with determining that the secondary microphone assembly of the first type is connected to the first boom connector, process the secondary microphone input signal according to a first primary processing scheme based on the secondary microphone assembly being of the first type and connected to the first boom connector.

In one or more exemplary communication devices, to determine if one or more microphone criteria are met comprises to determine if a secondary microphone assembly of a first type (first secondary microphone assembly) is connected to the second boom connector of the hearing protection device, and in accordance with determining that the secondary microphone assembly of the first type is connected to the second boom connector, process the secondary microphone input signal according to a first secondary processing scheme based on the secondary microphone assembly being of the first type and connected to the second boom connector.

In one or more exemplary communication devices, to determine if one or more microphone criteria are met comprises to determine if a secondary microphone assembly of a second type (second secondary microphone assembly) is connected to the first boom connector of the hearing protection device, and in accordance with determining that the secondary microphone assembly of the second type is connected to the first boom connector, process the secondary microphone input signal according to a second primary processing scheme based on the secondary microphone assembly being of the second type and connected to the first boom connector.

In one or more exemplary communication devices, to determine if one or more microphone criteria are met comprises to determine if a secondary microphone assembly of a second type (second secondary microphone assembly) is connected to the second boom connector of the hearing protection device, and in accordance with determining that the secondary microphone assembly of the second type is connected to the second boom connector, process the secondary microphone input signal according to a second secondary processing scheme based on the secondary microphone assembly being of the second type and connected to the second boom connector.

To process the secondary microphone input signal may comprise applying noise reduction, e.g. impulse noise reduction and/or broadband noise reduction, to the secondary microphone input signal. Applying noise reduction to the secondary microphone input signal may comprise applying noise reduction to selected frequency bands, such as one, two, three, or more frequency bands, of the secondary microphone input signal.

To process the secondary microphone input signal according to a processing scheme may comprise applying noise reduction, e.g. impulse noise reduction and/or broadband noise reduction, to the secondary microphone input signal. Different noise reduction schemes may be applied for different processing schemes.

In one or more exemplary communication devices, the processor may be configured to receive an input audio signal via the radio interface, e.g. via the third connector; and form the first output signal and/or the second output signal based on the input audio signal. The processor may be configured to process the input audio signal for provision of a first secondary output signal forming at least a part of the first output signal based on the input audio signal and/or for provision of a second secondary output signal forming at least a part of the second output signal based on the input audio signal. To process the input audio signal and/or to form the first output signal and/or the second output signal based on the input audio signal may comprise applying noise reduction, e.g. impulse noise reduction and/or broadband noise reduction, to the input audio signal. Applying noise reduction to the input audio signal may comprise applying noise reduction to selected frequency bands, such as one, two, three, or more frequency bands, of the input audio signal.

Accordingly, the processor may comprise a communication module configured for provision of a first secondary output signal forming at least part of the first output signal for the first receiver based on input audio signal from the radio interface. The input audio signal may be used directly as the first secondary output signal or processed, e.g. noise-reduced, to form the first secondary output signal. The communication module is optionally configured for provision of second secondary output signal forming at least part of second output signal for the second receiver based on the input audio signal. The input audio signal may be used directly as the second secondary output signal or processed, e.g. noise-reduced, to form the second secondary output signal. The communication module may be configured to provide an output audio signal for the radio unit/communication system/intercom system based on the secondary microphone input signal. The secondary microphone input signal may be fed directly to the radio interface as output audio signal or optionally processed, e.g. noise-reduced, in a voice processing module of the communication module. The voice processing module may be configured to filter and/or amplify the secondary microphone input signal for provision of the output audio signal. Accordingly, the communication module may comprise a voice processing module configured to process the secondary microphone input signal to form the output audio signal. The voice processing module may comprise a noise reduction module for applying noise-reduction to the secondary microphone input signal. In the communication module, to process the secondary microphone input signal may comprise applying noise reduction to the secondary microphone input signal. Applying noise reduction to the secondary microphone input signal optionally comprises applying impulse noise reduction to the secondary microphone input signal. Applying noise reduction to the secondary microphone input signal may comprise applying broadband noise reduction to the secondary microphone input signal. Applying noise reduction to the secondary microphone input signal may comprise applying noise reduction to selected frequency bands, such as one, two, three, or more frequency bands, of the secondary microphone input signal.

The processor of the communication device may comprise a mixing module configured for provision of the first output signal based on the first primary output signal from the hear-through processing module, and the first secondary output signal from the communication module, e.g. by addition and/or a linear combination of the first primary output signal and the first secondary output signal. Further, the mixing module may be configured for provision of the second output signal based on the second primary output signal from the hear-through processing module, and the second secondary output signal from the communication module, e.g. by addition and/or a linear combination of the second primary output signal and the second secondary output signal.

FIG. 1 shows an exemplary hearing protection system. The hearing protection system 2 comprises a hearing protection device 4 and a communication device 6. The hearing protection device 4, see also FIG. 5, comprises a first connector 8; a first ear protector 10; and a second ear protector 12. The first ear protector 10 comprises a first sound attenuation body 14A, a first primary microphone 16, and a first receiver 18, wherein the first primary microphone 16 and the first receiver 18 are electrically connected to a first primary terminal and a first receiver terminal of the first connector 8, respectively, i.e. the first primary microphone 16 is electrically connected to a first primary terminal of the first connector 8 and the first receiver 18 is electrically connected to a first receiver terminal of the first connector 8. The first sound attenuation body 14A is configured to cover an outer ear of a user.

The second ear protector 12 comprises a second sound attenuation body 14B, a second primary microphone 20, and a second receiver 22, wherein the second primary microphone 20 and the second receiver 22 are electrically connected to a second primary terminal and a second receiver terminal of the first connector 8, respectively, i.e. the second primary microphone 20 is electrically connected to a second primary terminal of the first connector 8 and the second receiver 22 is electrically connected to a second receiver terminal of the first connector 8. The second sound attenuation body 14B is configured to cover an outer ear of a user. A cable 23 connects microphones and receivers of first ear protector 10, 10A, second ear protector 12, 12A and microphone device 24 to the first connector 8 arranged at a distal end 23A of the cable 23.

The hearing protection device 4 comprises a secondary microphone device 24 electrically connected to a secondary terminal of the first connector, the secondary microphone device configured for picking up own voice of a user of the hearing protection device. The hearing protection device 4 comprises a microphone boom 26 with a distal end 28, and the secondary microphone device 24 is arranged at the distal end 28 of the microphone boom 26.

In hearing protection device 4, the first ear protector 10 comprises a first cushion 30 configured to encircle an outer ear of the user, and the second ear protector 12 comprises a second cushion 32 configured to encircle an outer ear of the user. The hearing protection device 4 comprising a headband 34, wherein the first ear protector 10 and the second ear protector 12 are connected to respective first end 36 and second end 38 of the headband 34.

The communication device 6 comprises a processor 50, 50A and an interface, the interface comprising a hearing protection device interface 52 for connection to hearing protection device 4; a user interface 54 including one or more buttons, such as a first button 56; and a radio interface 58 including a third connector 60 for connecting to and communicating with a radio unit 70 or communication system/intercom system via cable 72. The processor 50, 50A is wired to respective terminals of the hearing protection device interface 52; the user interface 54; and the radio interface 58.

The third connector 60 comprising a power terminal (not shown) for provision of power to the communication device 6 from a power unit, e.g. a battery (not shown), of the radio unit 70 connected to the third connector 60. The hearing protection device interface 52 includes a second connector 74, 74A comprising terminals configured for mating with respective terminals of the first connector 8, 8A of the hearing protection device 4. When the hearing protection device 4 is connected to the communication device 6, the processor 50, 50A receives, via the second connector 74, a first primary microphone input signal 16A from the first primary microphone 16 of hearing protection device 4 and a second primary microphone input signal 20A from the second primary microphone 20 of hearing protection device 4. Further, the processor is configured to output a first output signal 18A for the first receiver 18 of hearing protection device 4, and to output a second output signal 22A for the second receiver 22 of hearing protection device 4. Further, when the hearing protection device 4 is connected to the communication device 6, the processor 50 optionally receives, via the second connector 74, a secondary microphone input signal 24A from the secondary microphone device of hearing protection device 4. Further, when the hearing protection device 4 is connected to the communication device 6, the processor 50A optionally receives, via the second connector 74A, a secondary microphone input signal 24A from the secondary microphone device of hearing protection device 4.

Figure 2:
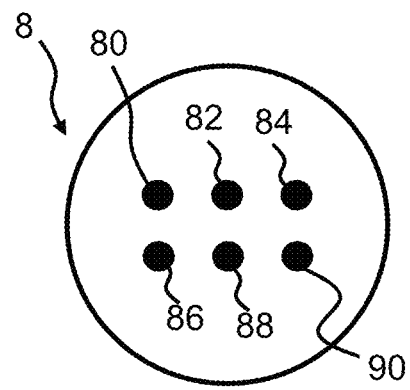
FIG. 2 is an end view of an exemplary first connector of the hearing protection device.

FIG. 2 is an end view of an exemplary first connector 8 of the hearing protection device 4. The first connector 8 comprises a first primary terminal 80, a first receiver terminal 82, a second primary terminal 84, and a second receiver terminal 86.

The first connector 8 may comprise a secondary terminal 88. The secondary terminal 88 is electrically connected to the secondary microphone device 24 configured for picking up own voice of a user of the hearing protection device. The first connector 8 comprises a reference terminal 90 also denoted a ground terminal.

Figure 3:
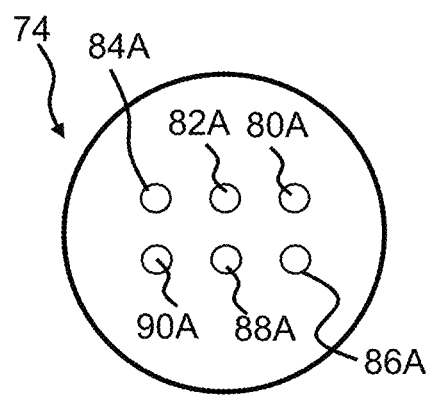
FIG. 3 is an end view of an exemplary second connector of the communication device.

FIG. 3 is an end view of an exemplary second connector 74 of the communication device 6. The second connector 74 comprises a first primary terminal 80A, a first receiver terminal 82A, a second primary terminal 84A, and a second receiver terminal 86A. The terminals 80A, 82A, 84A, 86A are configured for mating with respective terminals 80, 82, 84, 86 of the first connector 8 of the hearing protection device 4.

The second connector 74 may comprise a secondary terminal 88A. The secondary terminal 88A is electrically connected to the processor 50 for feeding secondary microphone input signal 24A from secondary microphone device 24 to the processor 50.

The second connector 74 comprises a reference terminal 90A also denoted a ground terminal.

Figure 4:
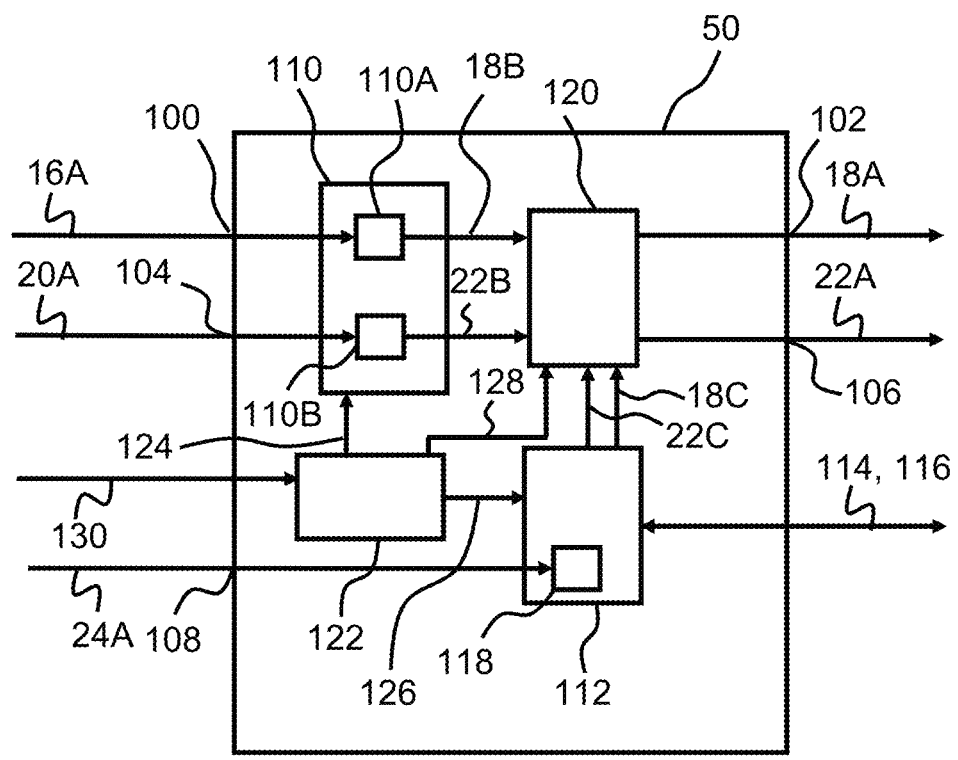
FIG. 4 is a schematic block diagram of a processor of an exemplary communication device, FIG. 5 schematically illustrates an exemplary hearing protection device.

FIG. 4 shows a schematic block diagram of a processor of an exemplary communication device 6. The processor 50 has a first primary input 100 electrically connected to first primary terminal 80A of second connector 74 and configured to receive first primary microphone input signal 16A from the first primary microphone 16 of hearing protection device 4. The processor 50 has a first receiver output 102 electrically connected to first receiver terminal 82A of second connector 74 and configured to output first output signal 18A to the first receiver 18 of hearing protection device 4. The processor 50 has a second primary input 104 electrically connected to second primary terminal 84A of second connector 74 and configured to receive second primary microphone input signal 20A from the second primary microphone 20 of hearing protection device 4. The processor 50 has a second receiver output 106 electrically connected to second receiver terminal 86A of second connector 74 and configured to output second output signal 22A to the second receiver 22 of hearing protection device 4. The processor 50 has a secondary input 108 electrically connected to secondary terminal 88A of second connector 74 and configured to receive secondary microphone input signal 24A from the secondary microphone device 24 of hearing protection device 4.

The processor 50 is configured to process the first primary microphone input signal 16A for provision of a first output signal 18A for the first receiver based on the first primary microphone input signal 16A; and output the first output signal 18A to the first receiver terminal 82A of the second connector.

The processor 50 comprises hear-through processing module 110 for performing hear-through processing of the first primary microphone input signal 16A and the second primary microphone input signal 20A. The hear-through processing module 110 comprises first noise reduction module 110A for performing noise reduction, such as impulse noise reduction, on the first primary microphone input signal 16A for provision of a first primary output signal 18B forming at least part of first output signal 18A for the first receiver 18 based on the first primary microphone input signal 16A. The hear-through processing module 110 comprises second noise reduction module 110B for performing noise reduction, such as impulse noise reduction, on the second primary microphone input signal 20A for provision of second primary output signal 22B forming at least part of second output signal 22A for the second receiver 22 based on the second primary microphone input signal 20A.

The processor 50 comprises communication module 112 for provision of first secondary output signal 18C forming at least part of first output signal 18A for the first receiver 18 based on an input audio signal 114 received from the radio unit 70 via third connector 60 of radio interface 58. Further, the communication module 112 is configured for provision of second secondary output signal 22C forming at least part of second output signal 22A for the second receiver 22 based on the input audio signal 114. The communication module 112 is optionally configured to provide an output audio signal 116 for the radio unit 70 via third connector 60 of radio interface 58 based on the secondary microphone input signal 24A. The secondary microphone input signal 24A may be fed directly to the radio interface as output audio signal 116 or optionally processed in voice processing module 118. The voice processing module is optionally configured to filter and/or amplify the secondary microphone input signal 24A for provision of the output audio signal. In one or more exemplary processors, the input audio signal 114 from the radio interface is fed directly to mixer.

The processor 50 comprises mixing module 120 for provision of the first output signal 18A based on the first primary output signal 18B and the first secondary output signal 18C, e.g. by addition and/or a linear combination of the first primary output signal 18B and the first secondary output signal 18C. Further, the mixing module 114 is optionally configured for provision of the second output signal 22A based on the second primary output signal 22B and the second secondary output signal 22C, e.g. by addition and/or a linear combination of the second primary output signal 22B and the second secondary output signal 22C.

The processor 50 optionally comprises controller 122 configured to control one or more of hear-through processing module 110 (via control signal 124), communication module 112 (via control signal 126) and mixing module 120 (via control signal 128), e.g. based on user input signal 130 from the user interface 54. For example, the communication module may be controlled to only feed the secondary microphone input signal 24A as the output audio signal 116 if the user input signal 130 is indicative of a user activating the first button 56 (push-to-talk function). The user input signal from the user interface may be fed to the third connector to enable control of the radio unit 70. In one or more exemplary communication devices, the control signal 124 controls, e.g. sets and/or adjusts, one or more noise reduction parameters, such as one or more filter coefficients, of noise reduction modules 110A, 110B. In one or more exemplary communication devices, the control signal 126 controls, e.g. sets and/or adjusts, one or more voice processing parameters, such as one or more filter coefficients and/or one or more gains of voice processing module 118. In one or more exemplary communication devices, the control signal 128 controls, e.g. sets and/or adjusts, one or more mixing parameters, such as one or more gain coefficients and/or weights, of mixing module 120.

The processor 50 is powered from the radio unit 70 or communication system/intercom system via a power terminal of the third connector 60 comprising a power terminal for provision of power to the communication device from a radio unit connected to the third connector.

Accordingly, the processor 50 is configured to receive a first primary microphone input signal 16A from the first primary microphone 16; process, with the hear-through processing module 110 and mixing module 120, the first primary microphone input signal 16A for provision of a first output signal 18A for the first receiver based on the first primary microphone input signal 16A; and output the first output signal 18A to a first receiver terminal of the second connector.

Figure 5:
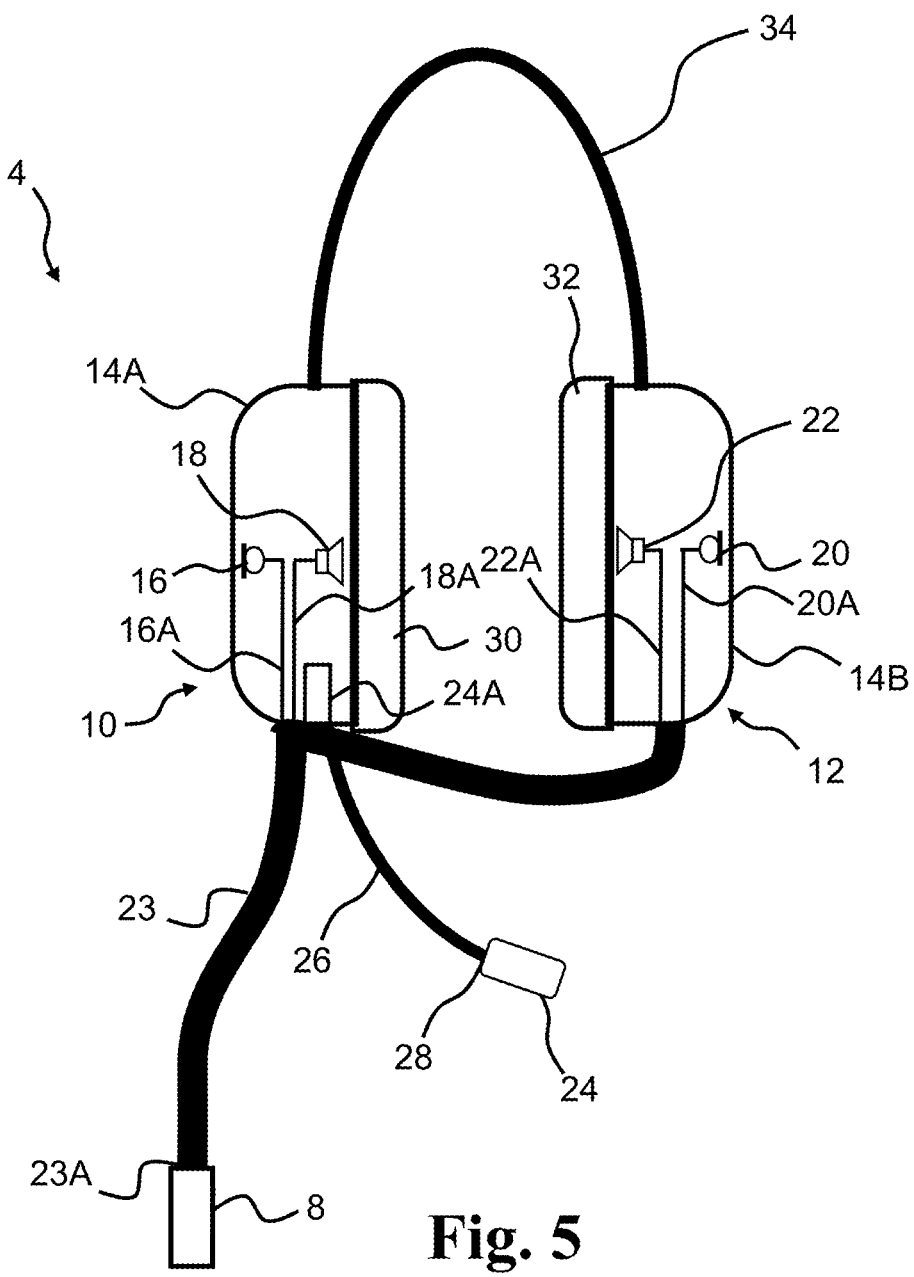

FIG. 5 schematically illustrates hearing protection device 4 and components thereof. A cable with conductors connect terminals of first connector 8 with respective microphones 16, 20, 24 and receivers 18, 22. In one or more exemplary hearing protection devices, the first connector is arranged near or in an ear protector, and the first connector and second connector are connected via a cable with connectors for mating with the first and second connector, respectively.

Figure 6:
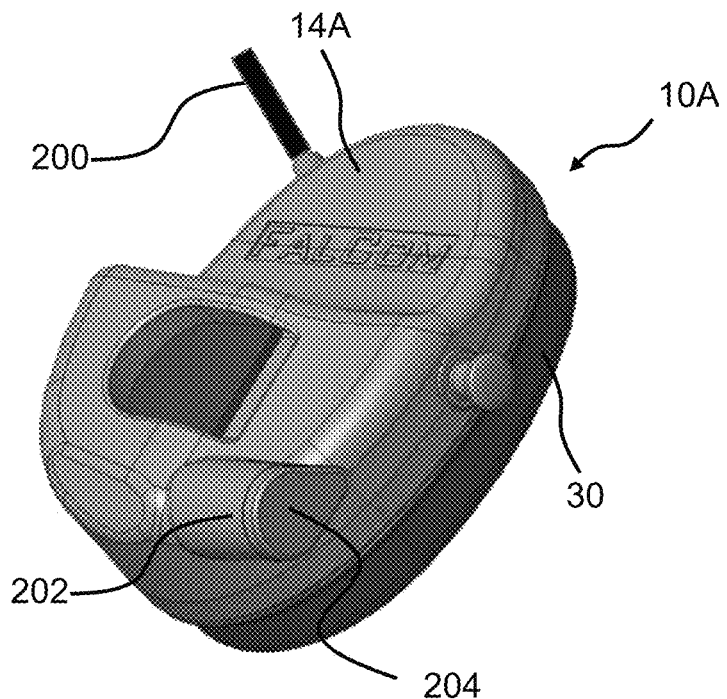
FIG. 6 is a perspective view of an exemplary first ear protector of one or more exemplary hearing protection devices.

FIG. 6 shows an exemplary first ear protector 10A of a hearing protection device such as hearing protection device 4. The first ear protector 10A comprises a first sound attenuation body 14A, a first primary microphone (not shown), and a first receiver (not shown), wherein the first primary microphone and the first receiver are electrically connected to a first primary terminal and a first receiver terminal of a first connector of the hearing protection device, respectively, i.e. the first primary microphone is electrically connected to a first primary terminal of the first connector and the first receiver is electrically connected to a first receiver terminal of the first connector 8. The first sound attenuation body 14A is configured to cover an outer ear of a user. A first cushion 30 of the first ear protector 10A ensures a tight fit to the user's head. A cable 200 connects the first ear protector to a second ear protector of the hearing protection device. The cable 200 comprises electrical conductors or wires electrically connecting the first primary microphone and the first receiver to a first primary terminal and a first receiver terminal of a first connector of the hearing protection device, respectively, see also FIG. 8.

The first ear protector 10A optionally comprises a first boom connector 202 for connecting a secondary microphone assembly (via connector of secondary microphone assembly) to the first ear protector. In the illustrated first ear protector 10A, a connector opening of the first boom connector 202 is covered and optionally sealed by a cover plate 204 or protective plug for protecting terminals of the first boom connector 202 from debris and/or moisture. The first boom connector 202 may be a female connector, a male connector, or a combined female and male connector.

The first boom connector 202 comprises a guide member embodied as a threaded cavity for accommodating a fixing member, such as a screw, in order to fix the secondary microphone assembly in a correct position on the first ear protector. The first boom connector 202 comprises a reference (ground) terminal and a first microphone terminal respectively connected to reference terminal and first secondary terminal of the first connector via cable 200.

Figure 7:
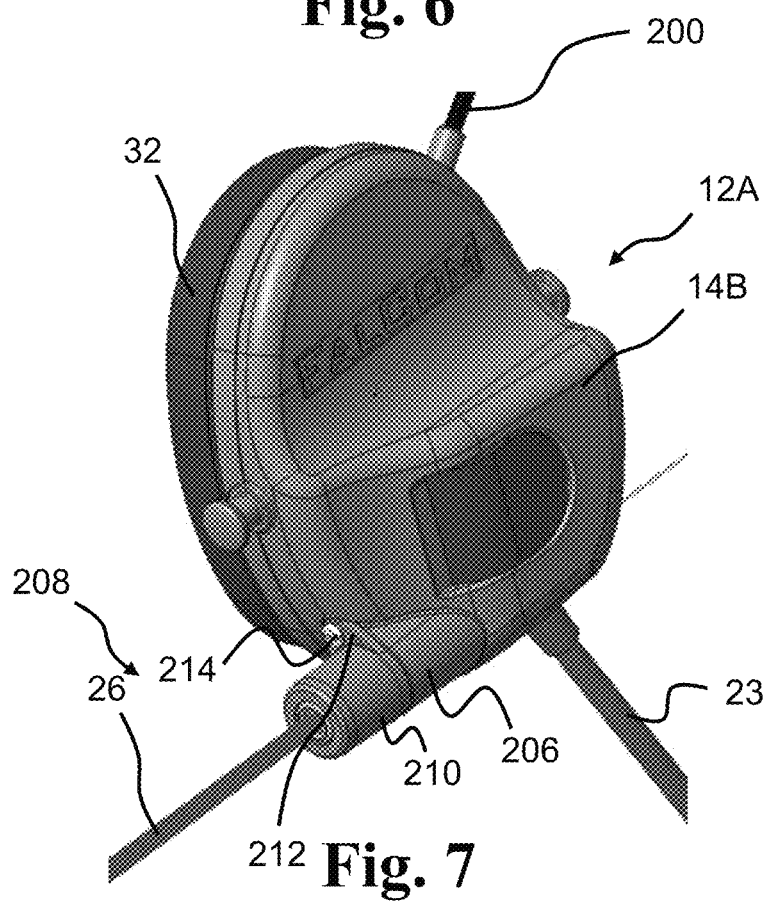
FIG. 7 is a perspective view of an exemplary second ear protector of one or more exemplary hearing protection devices.

FIG. 7 shows an exemplary second ear protector 12A of a hearing protection device such as hearing protection device 4. The second ear protector 12A comprises a second sound attenuation body 14B, a second primary microphone (not shown), and a second receiver (not shown), wherein the second primary microphone and the second receiver are electrically connected to a second primary terminal and a second receiver terminal of the first connector of the hearing protection device, respectively, i.e. the second primary microphone is electrically connected to a second primary terminal of the first connector and the second receiver is electrically connected to a second receiver terminal of the first connector. The second sound attenuation body 14B is configured to cover an outer ear of a user. A second cushion 32 of the second ear protector 12A ensures a tight fit to the user's head. Cable 200 connects the second ear protector to a first ear protector, such as first ear protector 10A, of the hearing protection device. A cable 23 connects microphones and receivers of first ear protector, second ear protector and microphone terminals of boom connectors to terminals of the first connector (not shown) arranged at a distal end of the cable 23. In one or more exemplary hearing protection devices, proximal end of the cable 23 is connected to the first ear protector.

The second ear protector 12A optionally comprises a second boom connector 206 for connecting a secondary microphone assembly 208 to the second ear protector 12A. In the illustrated second ear protector 12A, a secondary microphone assembly 208 comprising a microphone boom 26, a secondary microphone device (not shown), and a connector 210 is connected to the second ear protector 12A by mating the second boom connector 206 and the connector 210 of second microphone assembly 208. The connector 210 comprises a flange 212 with an opening acting as a guide member together with a threaded cavity of the second boom connector 206 for accommodating a fixing member, such as a screw 214, in order to fix the secondary microphone assembly 208 in a correct position on the second ear protector 12A.

The second boom connector 206 comprises a reference (ground) terminal and a first microphone terminal respectively connected to reference terminal and second secondary terminal of the first connector via cable 23. Further, cable 23 connects reference (ground) terminal and a first microphone terminal of the first boom connector to reference terminal and first secondary terminal of the first connector.

Figure 8:
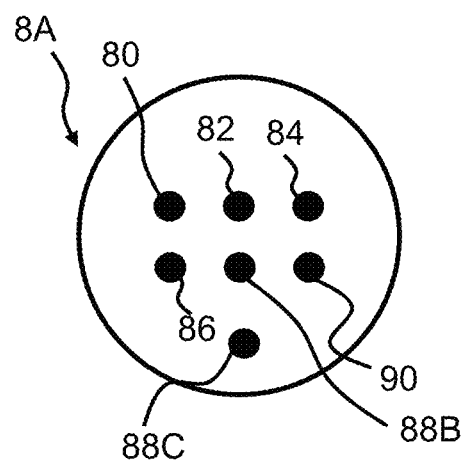
FIG. 8 is an end view of an exemplary first connector of the hearing protection device

FIG. 8 is an end view of an exemplary first connector 8A of the hearing protection device 4 comprising first ear protector 10A and second ear protector 12A. The first connector 8A comprises a first primary terminal 80, a first receiver terminal 82, a second primary terminal 84, and a second receiver terminal 86.

The first connector 8a may comprise a first secondary terminal 88B. The first secondary terminal 88B is electrically connected to first microphone terminal of first boom connector 202 for picking up own voice of a user of the hearing protection device when secondary microphone assembly 208 is connected to the first ear protector 10A. The first connector 8a may comprise a second secondary terminal 88C. The second secondary terminal 88C is electrically connected to first microphone terminal of second boom connector 206 for picking up own voice of a user of the hearing protection device when secondary microphone assembly 208 is connected to the second ear protector 12A. The first connector 8A comprises a reference terminal 90 also denoted a ground terminal.

Figure 9:
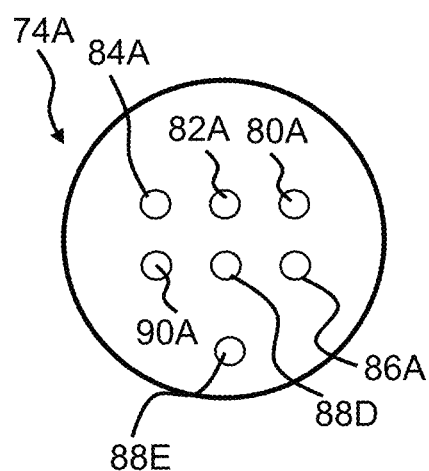
FIG. 9 is an end view of an exemplary second connector of the communication device.

FIG. 9 is an end view of an exemplary second connector 74A of the communication device 6. The second connector 74A comprises a first primary terminal 80A, a first receiver terminal 82A, a second primary terminal 84A, and a second receiver terminal 86A. The terminals 80A, 82A, 84A, 86A are configured for mating with respective terminals 80, 82, 84, 86 of the first connector 8A of the hearing protection device 4.

The second connector 74A may comprise a first secondary terminal 88D. The first secondary terminal 88D is electrically connected to the processor 50A for feeding secondary microphone input signal 24A from a secondary microphone assembly to the processor 50A when the secondary microphone device is connected to the first boom connector. The second connector 74A may comprise a second secondary terminal 88E. The second secondary terminal 88E is electrically connected to the processor 50A for feeding secondary microphone input signal 24A from a secondary microphone assembly to the processor 50A when the secondary microphone device is connected to the second boom connector. The second connector 74A comprises a reference terminal 90A also denoted a ground terminal.

Figure 10:
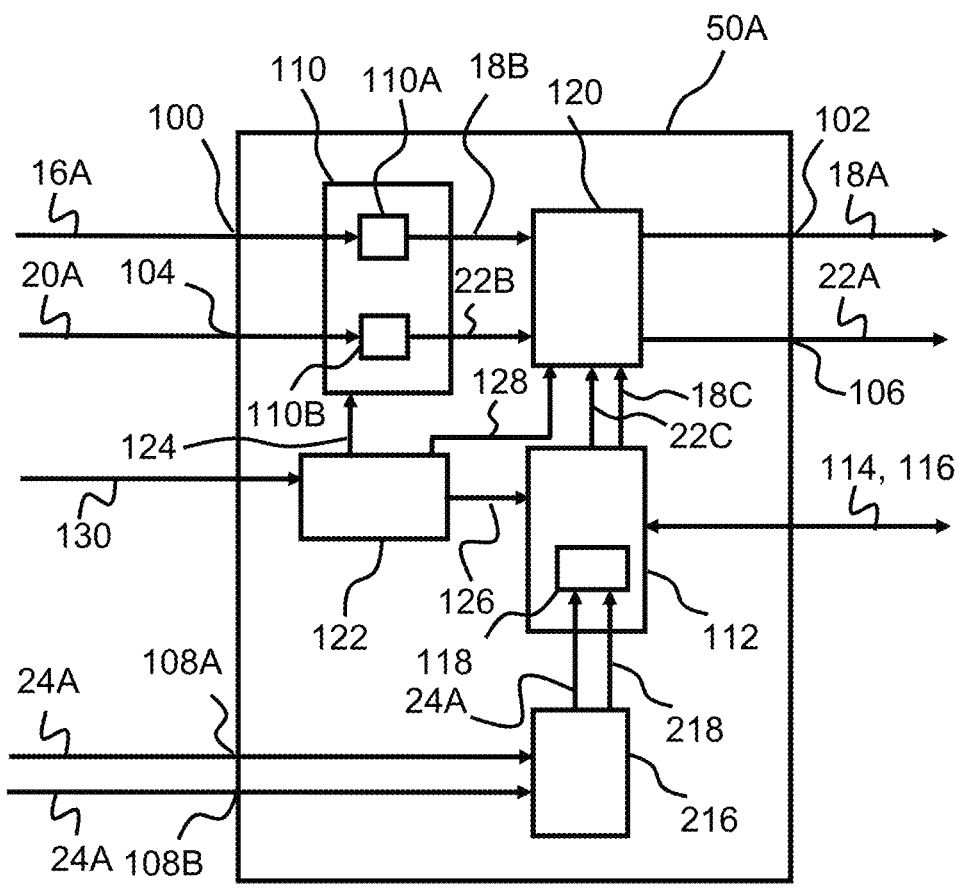
FIG. 10 is a schematic block diagram of a processor of an exemplary communication device.

FIG. 10 shows a schematic block diagram of a processor of an exemplary communication device 6. The processor 50A is similar to the processor 50 as described in relation to FIG. 4 and only differences between processor 50 and processor 50A will be described in the following.

The processor 50A has a first secondary input 108A electrically connected to first secondary terminal 88D of second connector 74A and configured to receive secondary microphone input signal 24A from the secondary microphone assembly 208 of hearing protection device 4 when the secondary microphone assembly 208 is connected to the first boom connector. The processor 50A optionally has a second secondary input 108B electrically connected to second secondary terminal 88E of second connector 74A and configured to receive secondary microphone input signal 24A from the secondary microphone assembly 208 of hearing protection device 4 when the secondary microphone assembly 208 is connected to the second boom connector.

The processor 50A comprises communication module 112 for provision of first secondary output signal 18C forming at least part of first output signal 18A for the first receiver 18 based on an input audio signal 114 received from the radio unit 70 via third connector 60 of radio interface 58. Further, the communication module 112 is configured for provision of second secondary output signal 22C forming at least part of second output signal 22A for the second receiver 22 based on the input audio signal 114.

The processor 50A is configured to determine if one or more microphone criteria are met, and, in accordance with one or more microphone criteria being satisfied, process the secondary microphone input signal for provision of an output audio signal based on the secondary microphone input signal; and output the output audio signal, e.g. to an audio terminal of the radio interface.

In an exemplary processor 50A, a determiner module 216 determines if a secondary microphone assembly is connected to the first boom connector of the hearing protection device e.g. by determining if a first impedance between the first secondary input 108A and refence satisfies a first connection criterion, e.g. if the first impedance is less than a first connection threshold. If the first connection criterion is satisfied, the determiner module 216 feeds or routes secondary microphone input signal 24A on first secondary input 108A to communication module 112 optionally for further processing of the secondary microphone input signal 24A.

Optionally, determiner module 216 determines if a secondary microphone assembly is connected to the second boom connector of the hearing protection device e.g. by determining if a second impedance between the second secondary input 108B and refence satisfies a second connection criterion, e.g. if the second impedance is less than a second connection threshold. If the second connection criterion is satisfied, the determiner module 216 feeds or routes secondary microphone input signal 24A on second secondary input 108B to communication module 112 optionally for further processing of the secondary microphone input signal 24A.

Optionally, determiner module 216 is configured to determine if the secondary microphone assembly connected to an ear protector is of a first type, and in accordance with determining that the secondary microphone assembly is of the first type (first secondary microphone assembly), the determiner module 216 optionally sends a first control signal via control line 218 to the communication module 112 that is configured to process the secondary microphone input signal 24A according to a first processing scheme associated with the first control signal from the determiner module 216.

Optionally, determiner module 216 is configured to determine if the secondary microphone assembly connected to an ear protector is of a second type, and in accordance with determining that the secondary microphone assembly is of the second type (second secondary microphone assembly), the determiner module 216 optionally sends a second control signal via control line 218 to the communication module 112 that is configured to process the secondary microphone input signal 24A according to a second processing scheme associated with the second control signal from the determiner module 216.

The communication module 112 is optionally configured to provide an output audio signal 116 for the radio unit 70 via third connector 60 of radio interface 58 based on the secondary microphone input signal 24A. The secondary microphone input signal 24A may be fed directly to the radio interface as output audio signal 116 or optionally processed in voice processing module 118 e.g. based on control signal on control line 218. The voice processing module 118 is optionally configured to filter and/or amplify the secondary microphone input signal 24A for provision of the output audio signal. In one or more exemplary processors, the input audio signal 114 from the radio interface is fed directly to mixer. A processing scheme may define filter coefficients and/or gains applied in the voice processing module.

In one of more exemplary processors, the control signal(s) from determiner module 216 are fed to the controller 122 configured to control one or more of hear-through processing module 110 (via control signal 124), communication module 112 (via control signal 126) and mixing module 120 (via control signal 128), e.g. based on control signal(s) from the determiner module 216. In one or more exemplary communication devices, the control signal 126 controls, e.g. sets and/or adjusts, one or more voice processing parameters, such as one or more filter coefficients and/or one or more gains of voice processing module 118 based on control signal(s) from the determiner module 216.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Exemplary hearing protection devices and hearing protection systems are disclosed in the following items.

Item 1. A hearing protection device comprising a first connector;

a first ear protector comprising a first sound attenuation body, a first primary microphone, and a first receiver, wherein the first primary microphone and the first receiver are electrically connected to a first primary terminal and a first receiver terminal of the first connector, respectively, and wherein the first sound attenuation body is configured to cover an outer ear of a user; and a second ear protector comprising a second sound attenuation body, a second primary microphone, and a second receiver, wherein the second primary microphone and the second receiver are electrically connected to a second primary terminal and a second receiver terminal of the first connector, respectively, and wherein the second sound attenuation body is configured to cover an outer ear of a user.

Item 2. Hearing protection device according to item 1, wherein the hearing protection device comprises a secondary microphone device electrically connected to a secondary terminal of the first connector, the secondary microphone device configured for picking up own voice of a user of the hearing protection device.

Item 3. Hearing protection device according to item 2, wherein the hearing protection device comprises a microphone boom with a distal end, and wherein the secondary microphone device is arranged at the distal end of the microphone boom.

Item 4. Hearing protection device according to any of items 1-3, wherein the hearing protection device is a passive hearing protection device.

Item 5. Hearing protection device according to any of items 1-4, wherein the first ear protector comprises a first cushion configured to encircle an outer ear of the user, and wherein the second ear protector comprises a second cushion configured to encircle an outer ear of the user.

Item 6. Hearing protection device according to any of item 1-5, wherein the first ear protector comprises a first attachment assembly, and wherein the second ear protector comprises a second attachment assembly, the first attachment assembly and the second attachment assembly each being configured for attachment to a helmet.

Item 7. Hearing protection device according to any of items 1-5, the hearing protection device comprising a headband, and wherein the first ear protector and the second ear protector are connected to respective first end and second end of the headband.

Item 8. Hearing protection system comprising a hearing protection device according to any of items 1-7 and a communication device comprising an interface including a second connector comprising terminals configured for mating with respective terminals of the first connector of the hearing protection device.

Item 9. Hearing protection system according to item 8, the interface comprising a user interface including one or more buttons; and a radio interface for connection with a radio unit and/or an intercom system.

Item 10. Hearing protection system according to any of items 8-9, wherein the communication device comprises a processor configured to:
receive a first primary microphone input signal from the first primary microphone;
process the first primary microphone input signal for provision of a first output signal for the first receiver based on the first primary microphone input signal; and
output the first output signal to a first receiver terminal of the second connector.

Item 11. Hearing protection system according to item 10, wherein to process the first primary microphone input signal comprises performing hear-through processing of the first primary microphone input signal.

Item 12. Hearing protection system according to any of items 10-11, wherein to process the first primary microphone input signal comprises applying noise reduction to the first primary microphone input signal.

Item 13. Hearing protection system according to item 12, wherein applying noise reduction to the first primary microphone input signal comprises applying impulse noise reduction to the first primary microphone input signal.

Item 14. Hearing protection system according to any of items 12-13, wherein applying noise reduction to the first primary microphone input signal comprises applying broadband noise reduction to the first primary microphone input signal.

Item 15. Hearing protection system according to any of items 12-14, wherein applying noise reduction to the first primary microphone input signal comprises applying noise reduction to selected frequency bands, such as one, two, three, or more frequency bands, of the first primary microphone input signal.

Item 16. Hearing protection system according to any of items 10-15, wherein the processor is configured to:
receive a second primary microphone input signal from the second primary microphone;
process the second primary microphone input signal for provision of a second output signal for the second receiver based on the second primary microphone input signal; and
output the second output signal to a second receiver terminal of the second connector.

Item 17. Hearing protection system according to item 16, wherein to process the second primary microphone input signal comprises performing hear-through processing of the second primary microphone input signal.

Item 18. Hearing protection system according to any of items 16-17, wherein to process the second primary microphone input signal comprises applying noise reduction to the second primary microphone input signal.

Item 19. Hearing protection system according to item 18, wherein applying noise reduction to the second primary microphone input signal comprises applying impulse noise reduction to the second primary microphone input signal.

Item 20. Hearing protection system according to any of items 18-19, wherein applying noise reduction to the second primary microphone input signal comprises applying broadband noise reduction to the second primary microphone input signal.

Item 21. Hearing protection system according to any of items 18-20, wherein applying noise reduction to the second primary microphone input signal comprises applying noise reduction to selected frequency bands, such as one, two, three, or more frequency bands, of the second primary microphone input signal.

Item 22. Hearing protection system according to any of items 10-21 as dependent on item 2 and item 9, wherein the processor is configured to:
receive a secondary microphone input signal from the secondary microphone device;
process the secondary microphone input signal for provision of an output audio signal based on the secondary microphone input signal; and
output the output audio signal to an audio terminal of the radio interface.

Item 23. Hearing protection system according to item 22, wherein to process the secondary microphone input signal comprises applying noise reduction to the secondary microphone input signal.

Item 24. Hearing protection system according to item 23, wherein applying noise reduction to the secondary microphone input signal comprises applying impulse noise reduction to the secondary microphone input signal.

Item 25. Hearing protection system according to any of items 23-24, wherein applying noise reduction to the secondary microphone input signal comprises applying broadband noise reduction to the secondary microphone input signal.

Item 26. Hearing protection system according to any of items 23-25, wherein applying noise reduction to the secondary microphone input signal comprises applying noise reduction to selected frequency bands, such as one, two, three, or more frequency bands, of the secondary microphone input signal.

Item 27. Hearing protection system according to any of items 10-26 as dependent on item 9, wherein the processor is configured to:
receive an input audio signal via the radio interface; and
form the first output signal based on the input audio signal.

Item 28. Hearing protection system according to item 27, wherein to form the first output signal based on the input audio signal comprises applying noise reduction to the input audio signal.

Item 29. Hearing protection system according to item 28, wherein applying noise reduction to the input audio signal comprises applying impulse noise reduction to the input audio signal.

Item 30. Hearing protection system according to any of items 28-29, wherein applying noise reduction to the input audio signal comprises applying broadband noise reduction to the input audio signal.

Item 31. Hearing protection system according to any of items 28-30, wherein applying noise reduction to the input audio signal comprises applying noise reduction to selected frequency bands, such as one, two, three, or more frequency bands, of the input audio signal.

Item 32. Hearing protection system according to any of items 8-31 as dependent on item 9, wherein the radio interface comprises a third connector comprising a power terminal for provision of power to the communication device from a radio unit connected to the third connector.

Item 33. Hearing protection device according to any of items 1-7, wherein the first ear protector comprises a first boom connector for connecting a secondary microphone assembly to the first ear protector.

Item 34. Hearing protection device according to item 33, wherein the second ear protector comprises a second boom connector for connecting a secondary microphone assembly to the second ear protector.

Item 35. Hearing protection device according to any of items 33-34, wherein the first boom connector comprises one or more guide elements.

Item 36. Hearing protection device according to item 35, wherein the one or more guide elements comprises a threaded cavity and/or a bajonet coupling part.

Item 37. Hearing protection device according to any of items 33-36 as dependent on claim 34, wherein the second boom connector comprises one or more guide elements.

Item 38. Hearing protection device according to item 37, wherein the one or more guide elements comprises a threaded cavity and/or a bajonet coupling part.

Item 39. Hearing protection device according to any of items 33-39, wherein the hearing protection device comprises a secondary microphone assembly, the secondary microphone assembly comprising a secondary microphone device and a connector for connecting the secondary microphone assembly to the first boom connector and/or the second boom connector.

Item 40. Hearing protection device according to item 39, wherein the connector of the secondary microphone assembly comprises one or more guide elements.

Item 41. Hearing protection device according to item 40, wherein the connector comprises a flange and the one or more guide elements comprises an opening in the flange.

Item 42. Hearing protection device according to any of items 33-41, wherein the first boom connector comprises one or more microphone terminals.

Item 43. Hearing protection device according to any of items 33-42 as dependent on claim 34, wherein the second boom connector comprises one or more microphone terminals.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing protection system
4 hearing protection device
6 communication device
8, 8A first connector
10, 10A first ear protector
12, 12A second ear protector
14A first sound attenuation body
14B second sound attenuation body
16 first primary microphone
16A first primary microphone input signal
18 first receiver
18A first output signal
18B first primary output signal
18C first secondary output signal
20 second primary microphone
20A second primary microphone input signal
22 second receiver
22A second output signal
22B second primary output signal
22C second secondary output signal
23 cable
23A distal end
24 secondary microphone device
24A secondary microphone input signal
26 microphone boom
28 distal end
30 first cushion
32 second cushion
34 headband
36 first end of headband
38 second end of headband
50, 50A processor
52 hearing protection device interface
54 user interface
56 first button
58 radio interface
60 third connector
70 radio unit
72 cable
74, 74A second connector
80 first primary terminal of first connector
80A first primary terminal of second connector
82 first receiver terminal of first connector
82A first receiver terminal of second connector
84 second primary terminal of first connector
84A second primary terminal of second connector
86 second receiver terminal of first connector
86A second receiver terminal of second connector
88 secondary terminal of first connector
88A secondary terminal of second connector
88B first secondary terminal of first connector
88C second secondary terminal of first connector
88D first secondary terminal of second connector
88E second secondary terminal of second connector
90 reference (ground) terminal of first connector
90A reference (ground) terminal of second connector
100 first primary input of processor
102 first receiver output of processor
104 second primary input of processor
106 second receiver output of processor
108 secondary input of processor
108A first secondary input of processor
108B second secondary input of processor
110 hear-through processing module
110A first noise reduction module
110B second noise reduction module
112 communication module
114 input audio signal
116 output audio signal
118 voice processing module
120 mixing module
122 controller
124 control signal
126 control signal 128 control signal
130 user input signal from user interface
200 cable
202 first boom connector
204 cover plate
206 second boom connector
208 secondary microphone assembly
210 connector of secondary microphone assembly
212 flange
214 fixing member, screw
216 determiner module

The invention claimed is:

1. A hearing protection system comprising a hearing protection device and a communication device, wherein the hearing protection device comprises:
   a first connector comprising terminals, the terminals comprising a first primary terminal, a first receiver terminal, a second primary terminal, and a second receiver terminal;
   a first ear protector comprising a first sound attenuation body, a first primary microphone, and a first receiver, wherein the first primary microphone and the first receiver are electrically connected to the first primary terminal and the first receiver terminal of the first connector, respectively, and wherein the first sound attenuation body is configured to cover an outer ear of a user;
   a second ear protector comprising a second sound attenuation body, a second primary microphone, and a second receiver, wherein the second primary microphone and the second receiver are electrically connected to the second primary terminal and the second receiver terminal of the first connector, respectively; and
   a secondary microphone device configured for picking up voice of the user of the hearing protection device;
   wherein the communication device is configured to receive a voice signal from the secondary microphone device of the hearing protection device, and to output a communication signal corresponding with the voice signal for reception by a receiving device, wherein the communication device comprises an interface including a second connector comprising terminals configured for respectively mating with the terminals of the first connector of the hearing protection device, the communication device comprising a processor configured to:
   receive a first primary microphone input signal from the first primary microphone, the first primary microphone input signal representing sound in an environment outside the first ear protector,
   process the first primary microphone input signal by applying noise reduction to the first primary microphone input signal to obtain a first output signal, and
   output the first output signal to one of the terminals of the second connector, the first output signal representing at least some of the sound in the environment outside the first ear protector.

2. The hearing protection system according to claim 1, wherein the secondary microphone device is electrically connected to a secondary terminal of the first connector.

3. The hearing protection system according to claim 1, further comprising a microphone boom with a distal end, and wherein the secondary microphone device is at a distal end of the microphone boom.

4. The hearing protection system according to claim 1, wherein the hearing protection device is a passive hearing protection device.

5. The hearing protection system according to claim 1, wherein the first sound attenuation body of the first ear protector comprises a first housing, wherein the second sound attenuation body of the second ear protector comprises a second housing, wherein the first ear protector comprises a first attachment assembly, and wherein the second ear protector comprises a second attachment assembly, the first attachment assembly and the second attachment assembly each being configured for attachment to a helmet.

6. The hearing protection system according to claim 1, wherein the communication device comprises a user interface including one or more buttons.

7. The hearing protection system according to claim 1, wherein the processor is configured to process the first primary microphone input signal by also performing hear-through processing of the first primary microphone input signal.

8. The hearing protection system according to claim 1, wherein the processor is configured to apply noise reduction to the first primary microphone input signal by applying impulse noise reduction to the first primary microphone input signal.

9. The hearing protection system according to claim 1, wherein the first ear protector comprises a first cushion having a circumferential portion defining a cavity for accommodating at least a part of the outer ear of the user.

10. A hearing protection system comprising a hearing protection device and a communication device, wherein the hearing protection device comprises:
   a first connector comprising terminals, the terminals comprising a first primary terminal, a first receiver terminal, a second primary terminal, and a second receiver terminal;
   a first ear protector comprising a first sound attenuation body, a first primary microphone, and a first receiver, wherein the first primary microphone and the first receiver are electrically connected to the first primary terminal and the first receiver terminal of the first connector, respectively, and wherein the first sound attenuation body is configured to cover an outer ear of a user; and
   a second ear protector comprising a second sound attenuation body, a second primary microphone, and a second receiver, wherein the second primary microphone and the second receiver are electrically connected to the second primary terminal and the second receiver terminal of the first connector, respectively;
   wherein the communication device comprises (1) an interface including a second connector comprising terminals configured for respectively mating with the terminals of the first connector of the hearing protection device, and (2) a radio interface for physically and detachably connection with a radio unit and/or an intercom system.

11. The hearing protection system according to claim 10, further comprising a secondary microphone device electrically connected to a secondary terminal of the first connector, the secondary microphone device configured for picking up voice of the user of the hearing protection device; wherein the communication device comprises a processor configured to:
   receive a secondary microphone input signal from the secondary microphone device;
   process the secondary microphone input signal for provision of an output audio signal based on the secondary microphone input signal; and output the output audio signal to an audio terminal of the radio interface.

12. The hearing protection system according to claim 10, wherein the processor is configured to:
receive an input audio signal via the radio interface; and
form an output signal based on the input audio signal.

13. The hearing protection system of claim 10, wherein the communication device comprises a processor configured to:
receive a first primary microphone input signal from the first primary microphone, the first primary microphone input signal represent sound in an environment outside the first ear protector;
process the first primary microphone input signal to obtain a first output signal; and
output the first output signal to one of the terminals of the second connector for transmission to the first receiver of the first ear protector, the first output signal representing at least some of the sound in the environment outside the first ear protector.

14. The hearing protection system of claim 10, wherein the first primary microphone of the first ear protector is configured to provide a first primary microphone input signal via the first primary terminal for processing by the communication device, the first primary microphone input signal representing sound in an environment outside the first ear protector, and wherein the first receiver of the first ear protector is configured to receive processed signal from the communication device via the first receiver terminal, and to provide output sound based on the processed signal, the output sound corresponding with at least some of the sound in the environment.

15. The hearing protection system of claim 14, wherein the processed signal received by the first receiver of the first ear protector represents the at least some of the sound in the environment.

16. The hearing protection system of claim 10, wherein the first primary terminal of the first connector and the first receiver terminal of the first connector have respective longitudinal axes that are offset from each other.

17. A hearing protection device for coupling with a communication device, the hearing protection device comprising:
a first connector configured to couple with the communication device, the first connector comprising terminals, the terminals comprising a first primary terminal, a first receiver terminal, a second primary terminal, and a second receiver terminal;
a first ear protector comprising a first sound attenuation body, a first primary microphone, and a first receiver, wherein the first primary microphone and the first receiver are electrically connected to the first primary terminal and the first receiver terminal of the first connector, respectively; and
a second ear protector comprising a second sound attenuation body, a second primary microphone, and a second receiver, wherein the second primary microphone and the second receiver are electrically connected to the second primary terminal and the second receiver terminal of the first connector, respectively;
wherein the first connector is configured to provide a first primary microphone input signal from the first primary microphone to the communication device, the first primary microphone input signal representing sound in the environment outside the first ear protector; and
wherein the first connector is also configured to receive a processed signal from the communication device, and wherein the first receiver is configured to provide output sound based on the processed signal, the processed signal representing at least some of the sound in the environment.

18. The hearing protection device according to claim 17, wherein the first ear protector comprises a first cushion configured to encircle a first outer ear of a user of the hearing protection device, and wherein the second ear protector comprises a second cushion configured to encircle a second outer ear of the user.

19. The hearing protection device according to claim 17, further comprising a headband, and wherein the first ear protector and the second ear protector are respectively connected to a first end and a second end of the headband.

20. The hearing protection device according to claim 17, further comprising a secondary microphone device configured for picking up voice of a user of the hearing protection device.

21. The hearing protection device according to claim 20, wherein the first ear protector comprises a first microphone connector configured to detachably couple with the secondary microphone device.

22. The hearing protection device according to claim 21, wherein the second ear protector comprises a second microphone connector configured to detachably couple with the second microphone device.

23. The hearing protection device according to claim 21, further comprising a cover configured to cover the first microphone connector when the secondary microphone device is not coupled with the first microphone connector.

24. The hearing protection device according to claim 17, wherein the first ear protector comprises a first cushion having a circumferential portion defining a cavity for accommodating at least a part of an outer ear of a user of the hearing protection device.

25. The hearing protection device according to claim 17, wherein the first sound attenuation body of the first ear protector comprises a housing and wherein the first ear protector also comprises an attachment device configured for attachment to a helmet.

26. The hearing protection device of claim 17, wherein the output sound provided by the first receiver of the first ear protector indicates the at least some of the sound in the environment attenuated by the first sound attenuation body.

27. The hearing protection device of claim 17, wherein the first primary terminal of the first connector and the first receiver terminal of the first connector have respective longitudinal axes that are offset from each other.

28. The hearing protection device of claim 17, wherein the first ear protector is configured to physically attenuate the sound in the environment, while the first receiver provides the output sound to allow a user of the hearing protection device to hear the sound in the environment.

29. A hearing protection system comprising the hearing protection device of claim 17 and the communication device, wherein the communication device is configured to receive the first primary microphone input signal representing sound in the environment from the first connector, process the first primary microphone input signal to obtain the processed signal, and provide the processed signal to the first connector, the processed signal representing the at least some of the sound in the environment.

30. The hearing protection system of claim 29, wherein the communication device comprises a first interface configured to physically and detachably couple with the first connector of the hearing protection device, and wherein the communication device comprises a second interface configured to physically and detachably couple with a radio unit and/or an intercom system.

31. A communication device configured to operate with a hearing protection device, the communication device comprising:
- a first interface configured to physically and detachably couple with the hearing protection device;
- a second interface configured to physically and detachably couple with a radio unit and/or an intercom system; and
- a processing unit configured to
  - receive a first microphone input signal from the hearing protection device, the first microphone input signal representing sound in an environment outside the hearing protection device,
  - process the first microphone input signal to obtain a first output signal, and
  - provide the first output signal to the first interface for transmission to the hearing protection device, the first output signal representing at least some of the sound in the environment outside the hearing protection device.

32. The communication device according to claim 31, wherein the processing unit is configured to:
- receive a second microphone input signal from the hearing protection device;
- process the second microphone input signal for provision of a second output signal; and
- provide the second output signal to the first interface for transmission to the hearing protection device.

33. The communication device according to claim 32, wherein the first output signal is for a first receiver of the hearing protection device, and the second output signal is for a second receiver of the hearing protection device.

34. The communication device according to claim 31, wherein the processing unit is configured to process the first microphone input signal by performing hear-through processing of the first microphone input signal.

35. The communication device according to claim 31, wherein the processing unit is configured to process the first microphone input signal by applying noise reduction to the first microphone input signal.

36. The communication device of claim 31, wherein the processing unit is configured to obtain a radio signal and provide the radio signal to the first interface for transmission to the hearing protection device.

37. The communication device of claim 36, wherein the processing unit of the communication device is configured to mix the radio signal and the first output signal to form a mixed signal, and wherein the processing unit of the communication device is configured to provide the first output signal and the radio signal by providing the mixed signal.

38. The communication device of claim 31, wherein the first interface comprises a first terminal for receiving the first microphone input signal representing the sound in the environment, and a second terminal for outputting the first output signal representing the at least some of the sound in the environment.

39. The communication device of claim 31, further comprising a user control, wherein the processing unit of the communication device is configured to obtain a secondary microphone signal from the hearing protection device via the first interface, the secondary microphone signal representing a voice of a user of the hearing protection device, and wherein the processing unit of the communication device is configured to provide the secondary microphone signal representing the voice of the user to the radio unit and/or the intercom system via the second interface in response to an actuation of the user control.

40. A hearing protection system comprising the communication device of claim 31 and a hearing protection device.

41. The hearing protection system of claim 40, wherein the hearing protection device comprises:
- a first connector configured to couple with the communication device, the first connector comprising terminals, the terminals comprising a first primary terminal, a first receiver terminal, a second primary terminal, and a second receiver terminal;
- a first ear protector comprising a first sound attenuation body, a first primary microphone, and a first receiver, wherein the first primary microphone and the first receiver are electrically connected to the first primary terminal and the first receiver terminal of the first connector, respectively; and
- a second ear protector comprising a second sound attenuation body, a second primary microphone, and a second receiver, wherein the second primary microphone and the second receiver are electrically connected to the second primary terminal and the second receiver terminal of the first connector, respectively;
- wherein the first connector is configured to provide a first primary microphone input signal from the first primary microphone to the communication device, the first primary microphone input signal representing sound in the environment outside the first ear protector; and
- wherein the first connector is also configured to receive a processed signal from the communication device, and wherein the first receiver is configured to provide output sound based on the processed signal, the processed signal representing at least some of the sound in the environment.

42. The hearing protection device of claim 41, wherein the output sound provided by the first receiver of the first ear protector indicates the at least some of the sound in the environment attenuated by the first sound attenuation body.

43. The hearing protection device of claim 41, wherein the first primary terminal of the first connector and the first receiver terminal of the first connector have respective longitudinal axes that are offset from each other.

44. The hearing protection device of claim 41, wherein the first ear protector is configured to physically attenuate the sound in the environment, while the first receiver provides the output sound to allow a user of the hearing protection device to hear the sound in the environment.

45. The hearing protection system of claim 41, further comprising a secondary microphone device configured for picking up voice of a user of the hearing protection device, and wherein the communication device is configured to provide voice signal representing the voice of the user to the radio unit and/or to the telecom system.

* * * * *